United States Patent
Melzi

(10) Patent No.: US 11,961,600 B2
(45) Date of Patent: Apr. 16, 2024

(54) SUPPLEMENTARY DEVICE FOR ATTACHMENT TO AN INJECTION DEVICE

(71) Applicant: SANOFI, Paris (FR)

(72) Inventor: Ilario Melzi, Milan (IT)

(73) Assignee: Sanofi, Paris (FR)

( * ) Notice: Subject to any disclaimer, the term of this patent is extended or adjusted under 35 U.S.C. 154(b) by 276 days.

(21) Appl. No.: 16/956,115

(22) PCT Filed: Dec. 18, 2018

(86) PCT No.: PCT/EP2018/085386
§ 371 (c)(1),
(2) Date: Jun. 19, 2020

(87) PCT Pub. No.: WO2019/121607
PCT Pub. Date: Jun. 27, 2019

(65) Prior Publication Data
US 2020/0327974 A1 Oct. 15, 2020

(30) Foreign Application Priority Data

Dec. 21, 2017 (EP) .................................. 17306874

(51) Int. Cl.
*G16H 20/17* (2018.01)
*A61M 5/168* (2006.01)
(Continued)

(52) U.S. Cl.
CPC .......... *G16H 20/17* (2018.01); *A61M 5/1684* (2013.01); *A61M 5/20* (2013.01); *G16H 40/67* (2018.01);
(Continued)

(58) Field of Classification Search
CPC .. A61M 2005/2006; A61M 2005/3126; A61M 2005/3125; A61M 5/1684;
(Continued)

(56) References Cited

U.S. PATENT DOCUMENTS

2010/0286612 A1* 11/2010 Cirillo ............... A61M 5/31525
700/282
2014/0276385 A1 9/2014 Buchine et al.
(Continued)

FOREIGN PATENT DOCUMENTS

CN 104220116 12/2014
CN 105167781 12/2015
(Continued)

OTHER PUBLICATIONS

PCT International Preliminary Report on Patentability in International Appln. No. PCT/EP2018/085386, dated Jun. 23, 2020, 7 pages.
(Continued)

*Primary Examiner* — Jenna Zhang
(74) *Attorney, Agent, or Firm* — Fish & Richardson P.C.

(57) ABSTRACT

A supplementary device configured to be releasably attached to an injection device includes at least one wireless communication unit and at least one sensor, wherein the supplementary device is configured to activate the at least one sensor in response to receipt via the at least one wireless communication unit of a wireless communication from an external device, following activation, to use the at least one sensor to detect the start of an injection by the injection device, and to communicate, via the at least one wireless communication unit, the start of the injection to the external device.

20 Claims, 12 Drawing Sheets

(51) Int. Cl.
  *A61M 5/20* (2006.01)
  *G16H 40/67* (2018.01)
  *A61M 5/31* (2006.01)

(52) U.S. Cl.
  CPC .............. *A61M 2005/2006* (2013.01); *A61M 2005/3125* (2013.01); *A61M 2205/3368* (2013.01); *A61M 2205/3553* (2013.01); *A61M 2205/3576* (2013.01)

(58) Field of Classification Search
  CPC ............ A61M 5/20; A61M 2205/3368; A61M 2205/3553; A61M 2205/3576; A61M 5/315; G16H 20/17; G16H 40/67
  See application file for complete search history.

(56) References Cited

U.S. PATENT DOCUMENTS

| | | | |
|---|---|---|---|
| 2014/0330243 | A1 | 11/2014 | Kietzmann et al. |
| 2016/0012205 | A1 | 1/2016 | Saint et al. |
| 2016/0067409 | A1* | 3/2016 | Blei .................. A61M 5/31 604/207 |
| 2016/0235925 | A1* | 8/2016 | Kuhn ................ A61M 5/31525 |
| 2017/0049965 | A1 | 2/2017 | Baker et al. |
| 2019/0192778 | A1* | 6/2019 | Rehbein .............. A61M 5/3155 |
| 2019/0201627 | A1* | 7/2019 | Helmer ............... A61M 5/2033 |

FOREIGN PATENT DOCUMENTS

| | | | | |
|---|---|---|---|---|
| EP | | 3058970 | 8/2016 | |
| JP | | 2005-253999 | 9/2005 | |
| JP | | 2016-189797 | 11/2016 | |
| JP | | 2017-522077 | 8/2017 | |
| JP | | 2017-524399 | 8/2017 | |
| WO | WO 2011/117212 | | 9/2011 | |
| WO | WO 2013/120777 | | 8/2013 | |
| WO | WO 2014/011740 | | 1/2014 | |
| WO | WO-2014011740 A1 * | | 1/2014 | ........... A61B 5/0002 |
| WO | WO 2015/185686 | | 12/2015 | |
| WO | WO 2015/187793 | | 12/2015 | |
| WO | WO 2016/193229 | | 12/2016 | |
| WO | WO-2016193229 A1 * | | 12/2016 | ........ A61M 5/31551 |
| WO | WO 2018/041798 | | 3/2018 | |
| WO | WO-2018041798 A1 * | | 3/2018 | ............ A61M 5/002 |

OTHER PUBLICATIONS

PCT International Search Report and Written Opinion in International Appln. No. PCT/EP2018/085386, dated Feb. 28, 2019, 10 pages.

* cited by examiner

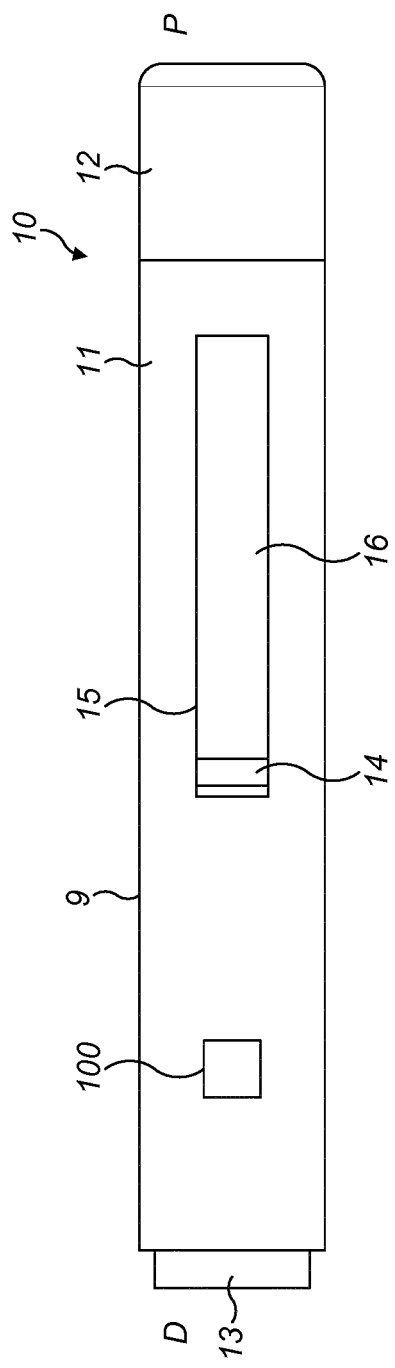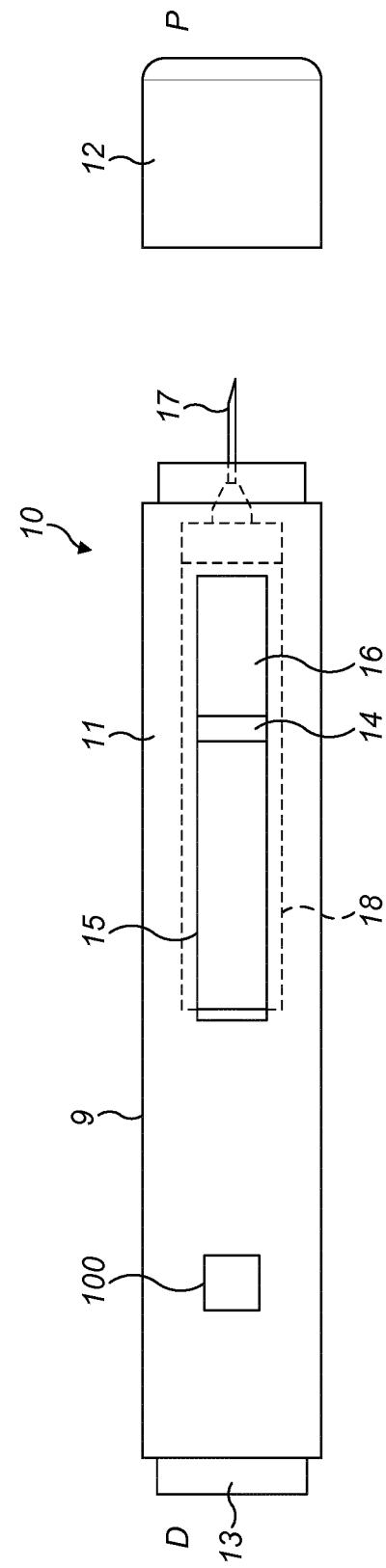

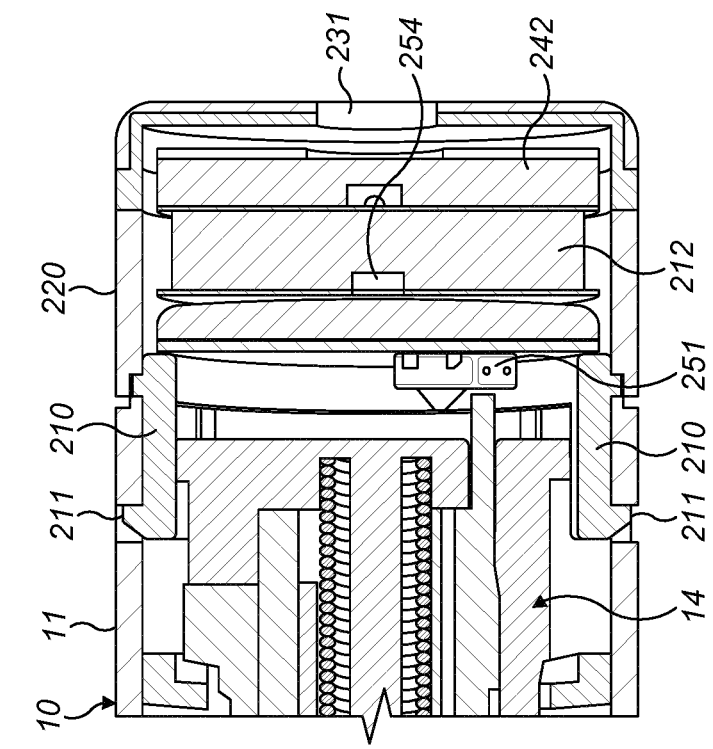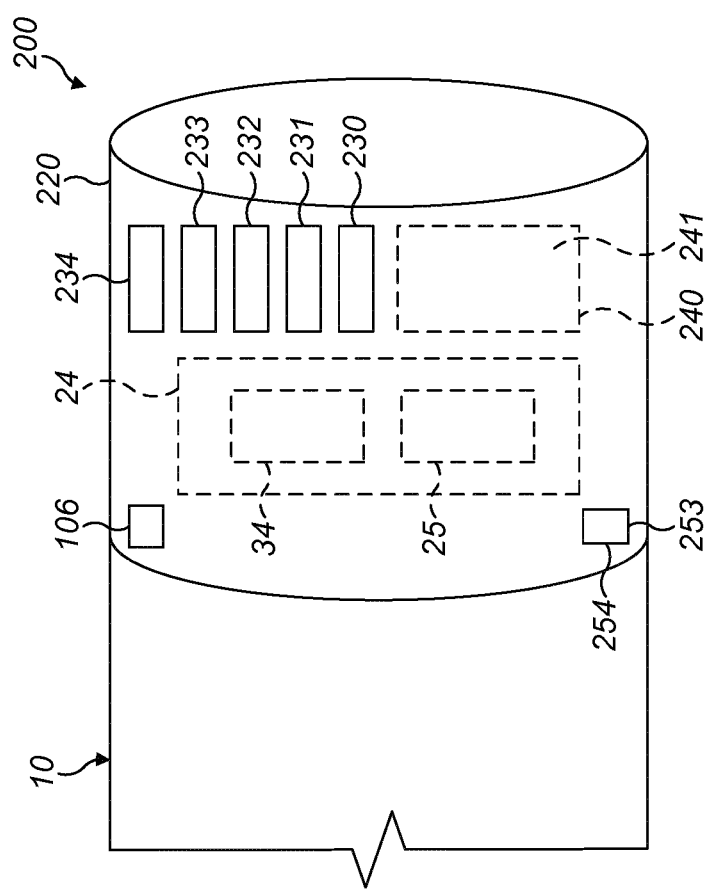
FIG. 3

SUPPLEMENTARY DEVICE FOR ATTACHMENT TO AN INJECTION DEVICE

CROSS REFERENCE TO RELATED APPLICATIONS

The present application is the national stage entry of International Patent Application No. PCT/EP2018/085386, filed on Dec. 18, 2018, and claims priority to Application No. EP 17306874.3, filed on Dec. 17, 2017, the disclosures of which are incorporated herein by reference.

TECHNICAL FIELD

This relates to a supplementary device configured to be releasably attached to an injection device.

BACKGROUND

Various diseases exist that require regular treatment by injection of a medicament. Such injection can be performed by using injection devices, which are applied either by medical personnel or by patients themselves.

Injection devices (i.e. devices capable of delivering medicaments from a medication container) aim to make self-administration of injected therapies easier for patients. Current therapies delivered by means of self-administered injections include drugs for diabetes (both insulin and newer GLP-1 class drugs), migraine, allergies, hormone therapies, anticoagulants etc. Injection devices can be used to deliver a single dose of a particular life-saving drug. For example they are often prescribed to people who are at risk for anaphylaxis. They are also often used in the military to protect personnel from chemical warfare agents. Alternatively, injection devices are used to administer medicaments according to a prescribed therapeutic schedule for people suffering from, for example, Multiple Sclerosis, Rheumatroid Arthritis, or Anemia.

Injection devices may be disposable or single use devices which may only be used to deliver one dose of medicament and which have to be disposed of after use. Other types of injection devices may be reusable. Usually they are arranged to allow a user to load and unload a standard syringe. The reusable injection device may be used to perform multiple parenteral drug deliveries, whereas the syringe is disposed after having been spent and unloaded from the injection device. The syringe may be packaged with additional parts to provide additional functionality. In a typical scenario a disease can be treated by patients themselves by injection of medicament doses using an injection device, for example on a daily, weekly, bi-weekly, or monthly basis.

Injection devices typically fall into two categories—manual devices and auto-injection devices.

In a manual device—the user must provide the mechanical energy to drive the fluid through the needle. This is typically done by some form of button/plunger that has to be continuously pressed by the user during the injection.

Auto-injection devices are devices which completely or partially replace activities involved in parenteral drug delivery from standard syringes. These activities may include insertion of a needle into a patient's skin, injection of the medicament, removal of the needle, shielding of the needle, and preventing reuse of the device. Auto-injection devices may lead to a reduction in: forces required of the user, problems with hand-shaking, and the likelihood of delivering an incomplete dose. Triggering may be performed by numerous means, for example a trigger button or the action of the needle reaching its injection depth. In some devices, the energy to deliver the fluid is provided by a spring.

Needleless injection devices have been developed which deliver medicament using needle-free injection technology. Such systems deliver medicament through the skin using mechanisms that do not involve the penetration of the skin with a cannula.

To prevent false handling of an injection device or to keep track of usage data, it is desirable to measure information related to a condition and/or use of the injection device. Re-usable add-on devices suitable for use with injectors and which monitor the dose delivered by the injectors (and provide other information to a user) are known. It has been described, for instance in WO 2011/117212 to provide a supplementary device comprising a mating unit for releasably attaching the device to an injection device. The device includes a camera and is configured to perform optical character recognition (OCR) on captured images visible through a dosage window of the injection pen, thereby to determine a dose of medicament that has been dialled into the injection device.

Improved add-on devices capable of determining and communicating usage information associated with injection devices are required. Methods for minimizing the power consumption of such add-on devices are required.

SUMMARY

There is provided a supplementary device 200, for attachment to an injection device 10, which is capable of determining and communicating usage information associated with an injection device 10 to an external device 1000. The supplementary device 200 is particularly advantageous when used with disposable injection devices, as it allows data to be recorded and stored separately from the injection device, which will be disposed, and allows the combination of usage data from multiple disposable devices for a single user.

According to an aspect of the disclosure, there is provided a supplementary device configured to be releasably attached to an injection device, the supplementary device comprising: at least one wireless communication unit; at least one sensor; wherein the supplementary device is configured: to activate the at least one sensor in response to receipt via the at least one wireless communication unit of a wireless communication from the external device; following activation, to use the at least one sensor to detect the start of an injection by the injection device; and to communicate via the at least one wireless communication unit the start of the injection to the external device.

The supplementary device may comprise an extension, and the at least one sensor may be positioned upon the extension. The extension may be a flexible printed circuit board.

The supplementary device may be configured to indicate that the start of an injection by the injection device has not been detected.

The supplementary device may be configured to indicate that the start of an injection by the injection device has been detected and that an end of the injection by the injection device has not been detected.

The supplementary device may be configured to indicate that the start of an injection by the injection device has been detected and that an end of the injection by the injection device has not been detected within a predetermined time of the start of the injection.

The supplementary device may be configured to indicate whether the communication to the external device was successful.

The supplementary device may further comprise a temperature sensor.

The supplementary device may be configured to indicate whether medicament included in the injection device meets a predetermined temperature parameter.

The supplementary device may be configured start a timer in response to determining that medicament included in the injection device does not meet a predetermined temperature parameter, and may provide an indication when the timer expires.

According to an aspect of the disclosure, there is provided a system comprising: any supplementary device defined herein, and an injection device, wherein the supplementary device is releasably attached to the injection device.

The injection device may be a disposable autoinjector.

The supplementary device may comprise a housing shaped so that, upon attachment to the injection device, the housing of the supplementary device is flush with the housing of the injection device.

The system may be of uniform width but greater longitudinal length than the injection device.

The supplementary device may be configured to attach within a recess located at the distal end of an injection device.

BRIEF DESCRIPTION OF THE FIGURES

FIG. 1A shows a side view of an injection device;

FIG. 1B shows a side view of the injection device of FIG. 1A with a cap detached;

FIG. 3 shows the internal components of an embodiment of the supplementary device attached to an injection device;

DETAILED DESCRIPTION

Figure 2A:
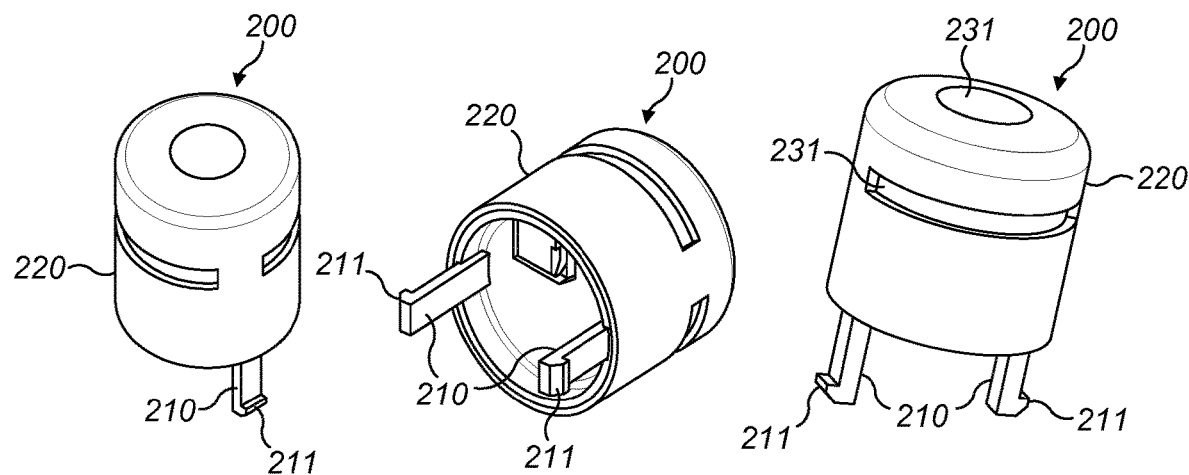
FIG. 2A shows external views of an embodiment of a supplementary device.

In the following, embodiments will be described with reference to a pen injector. The present disclosure is however not limited to such applications and may equally well be deployed with other types of drug delivery devices, such as syringes, pre-filled syringes, needleless injectors and inhalers.

An injection device 10 (also referred to herein as a drug delivery device 10) according to embodiments will now be described with reference to FIGS. 1A and 1B. In some embodiments, the injection device 10 is a single use injection device 10, such as an autoinjector. In some other embodiments, the injection device 10 is a re-usable injection device or an injection device which can be used to inject a number of doses before being discarded. The injection device 10 has a proximal end P and a distal end D. The proximal end P is directed towards the injection site of a patient during an injection while the distal end D is directed away from the injection site.

The injection device 10 comprises a body 9 and a cap 12 (also referred to herein as the outer needle cap 12 or ONC 12). The body 9 comprises an outer housing 11. The outer housing 11 is an elongate tube. The outer housing 11 includes a cartridge holder or syringe holder (not shown) which supports a cartridge or syringe 18 containing liquid medicament 16. Hereafter the description shall refer to a cartridge 18, which is supported by a cartridge holder (not shown). The cartridge 18 is shown in broken lines in FIG. 1B, and may be positioned under a window 15 in the housing 11.

The outer housing 11 also houses a dispense mechanism (not shown) for causing dispensing of the medicament 16 during injection.

A hollow needle 17 communicates with an interior volume of the cartridge 18 and serves as a conduit for liquid medicament 16 during injection. The needle 17 and the cartridge 18 are in a fixed position relative to each other and to the body 9. A stopper, plunger, piston or bung 14 is moveable within the cartridge 18 to as to expel medicament contained within the cartridge 18 through the needle 17 under action of the dispense mechanism.

The dispense mechanism is mechanically coupled to the piston 14 of cartridge 18. The dispense mechanism is configured to move the piston axially along the cartridge 18 in a proximal direction to dispense medicament 16 through the needle 17. The dispense mechanism includes components that cooperate to apply a force to the piston 14 in response to an actuation input provided by a user. Here, the actuation input that triggers application of a force to the piston 14 is received by way of a dose dispense button 13 that is located at the distal end of the injection device 10. The dispense mechanism is mechanically coupled to the dispense button 13.

A label is provided on the housing 11. The label includes information 100 about the medicament included within the injection device 10, including information identifying the medicament. The information 100 identifying the medicament may be in the form of text. The information 100 identifying the medicament may also be in the form of a colour. The information 100 identifying the medicament may also be encoded into a barcode, QR code or the like. The information 100 identifying the medicament may also be in the form of a black and white pattern, a colour pattern or shading.

Figure 2B:
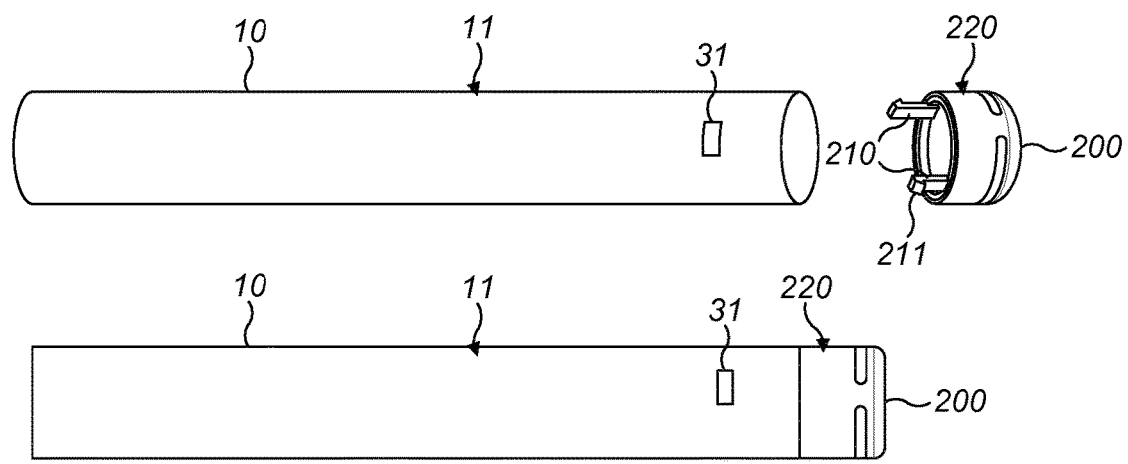
FIG. 2B shows an injection device with removed cap, an injection device with a supplementary device in the process of attachment, and an injection device with a supplementary device attached.

FIG. 2a is a schematic illustration of an embodiment of a supplementary device 200 for releasable attachment to injection device 10 of FIG. 1. FIG. 2b shows an injection device before, during, and after attachment to an embodiment of the supplementary device 200. The supplementary device 200 is suitable for use with the injection device shown in FIGS. 1A and 1B and other types of injection device as discussed above. The supplementary device 200 may be for use with an injection device, including both reusable injection devices and disposable injection devices. The supplementary device 200 may also be suitable for use with manual injectors and autoinjectors. In a particular embodiment, the supplementary device 200 may be for use with a disposable pen autoinjector.

The supplementary device 200 may be attachable to an injection device 10. For instance, the supplementary device 200 may comprise means for attaching 210 to an injection device, or the injection device may comprise means for attaching to the supplementary device 200. The supplementary device 200 may comprise means 210 configured to attach to a part of the injection device that has been configured for the attachment of the supplementary device 200. The injection device 10 and supplementary device 200 may optionally comprise co-operating alignment features to ensure that the supplementary device 200 is correctly orientated and positioned with respect to the injection device 10. In an illustrative example, the supplementary device 200 may comprise hooks 211, and the injection device may comprise recesses 31, wherein the hooks 211 of the supplementary device 200 are configured such that they are able to snap into place and hence allow the supplementary device 200 to be retained on the injection device. Other attachment means may include: adhesive surfaces, magnetic components, clips, threaded components, or any suitable means.

The injection device may comprise a cap 30, which is positioned in, on, or over the supplementary device 200 attachment location. This cap 30 may, for instance, comprise hooks similar to those of the supplementary device 200 and be attached in a similar manner. The cap 30 may be a removable cap that can be removed before attachment of the supplementary device 200.

The attachment means 210 may be such that the orientation, position, or alignment of the supplementary device 200 in relation to the injection device 10 is predetermined upon attachment. The predetermined orientation, position, or alignment may be such as to locate any features, such as sensors, in the correct place for their operation. For instance, the supplementary device 200 may comprise hooks 211 that engage with recesses 31 upon the injection device 10, and the hooks 211 and recesses 31 may be configured such that the supplementary device 200 can only be attached in a manner that allows the correct functioning of the device, for instance any sensors could be positioned in the optimal location for detection. The supplementary device 200 may attach to any part of the injection device 10, as long as the attachment does not interfere with the operation of the injection device 10. For instance, the injection device 10 may be an autoinjector and the supplementary device 200 may attach to the distal end of the autoinjector.

Supplementary device 200 includes a housing 220. The housing 220 may provide an outer cover for at least part of the supplementary device 200.

Optionally, the housing 220 of the supplementary device 200 may be shaped so that, upon attachment to the distal end of an injection device 10, the housing 220 of the supplementary device 200 is flush with the housing of the injection device 10, as illustrated by FIG. 2b. The attachment of the supplementary device 200 to the injection device 10 therefore leads to an assembly of uniform width but a longer length than the injection device 10 alone. To achieve this effect the supplementary device 200 may be shaped to have the same width or diameter as the lateral width or diameter of the injection device 10. Alternatively, or in addition, the housing 220 of the supplementary device 200 may be configured such that, upon attachment to the distal end of an injection device 10, the supplementary device housing 220 is parallel to, and level with, the injection device housing 11. The supplementary device housing 220 may have an edge configured so that, upon attachment to an injection device 10, at least a portion of the edge of the supplementary device housing 220 meets and matches at least a portion an edge of the injection device housing 11. In a particular embodiment, the entire of an edge of the supplementary device housing 220 is configured to meet and match the entire of an edge of the injection device housing 11, when the supplementary device 200 is attached to the injection device 10.

Alternatively, the supplementary device 200 may be configured to attach to be distal end of an injection device 10 and to be wider than the injection device 10, so that the resultant assembly is an injection device with a wider distal end.

Figure 13A:
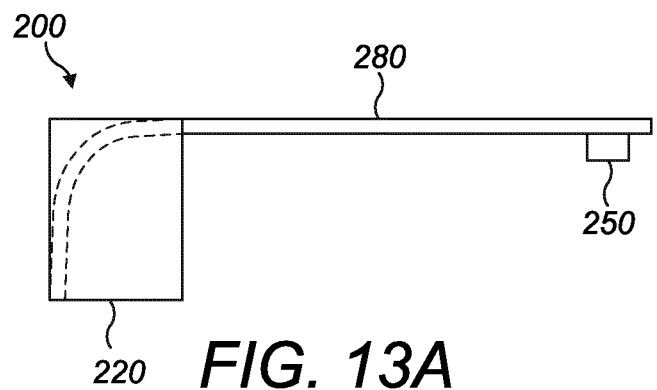
FIG. 13 shows embodiments of the supplementary device comprising an extension configured such that when the supplementary device is attached to the injection device the extension is located within a recess or cavity of the injection device.
Figure 13B:
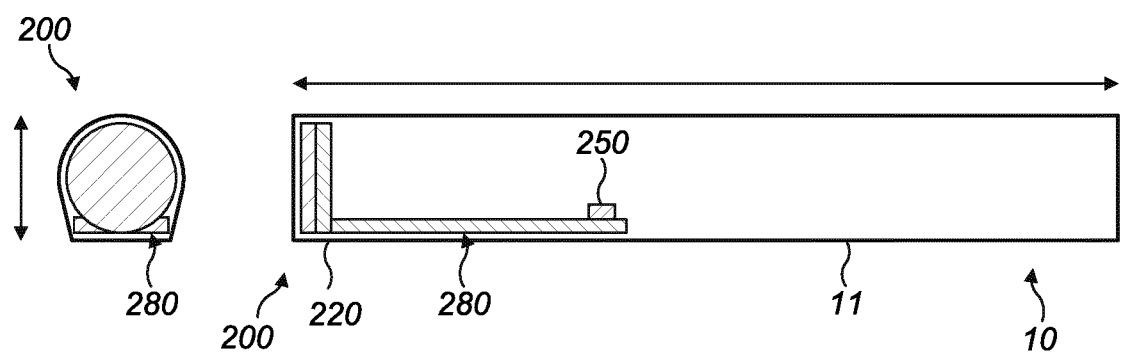
Figure 13C:
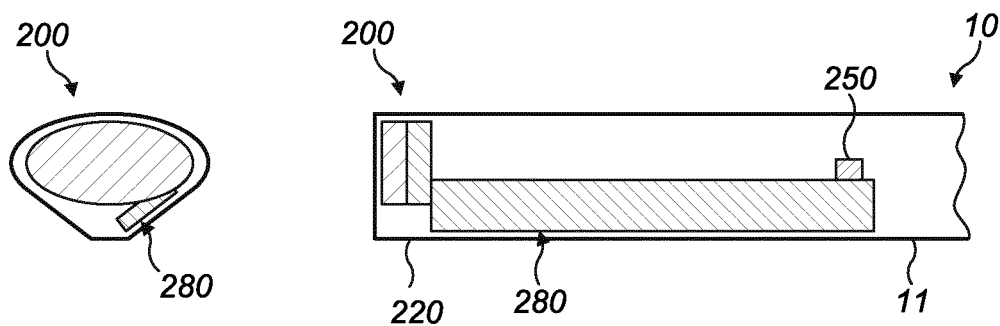

The supplementary device 200 may be shaped so that, upon attachment to an injection device 10, at least a part of the supplementary device 200 will extend into the injection device 10 (see FIG. 13A). This may, for instance, allow the positioning of sensors or components in a location to allow the determination of information in relation to the injection device 10. The part of the supplementary device 200 that extends into the injection device 10 may be a flexible or rigid extension 280, for instance a flexible printed circuit board (PCB) extension. The flexible or rigid extension 280 may be configured such that when the supplementary device 200 is attached to the injection device 10 the flexible or rigid extension 280 is located within a recess or cavity of the injection device 10 (FIG. 13B or FIG. 13C). This cavity or recess may be located such that it is covered by a removable cap 30 when said cap is attached to the injection device 10. The flexible or rigid extension 280 may have sensors, for instance a sensor 250 for detecting the start and end of an injection, the conductive rubber pad 260, the micro-switch 261, the optical reflecting sensor 263, optical sensor 254, or temperature sensor 255 discussed herein, which are positioned upon the extension 280 in such a manner as to enable them to perform their role (for instance, detecting the movement of a part of the injection device 10) when the supplementary device 200 is attached to the injection device 10.

In some embodiments, the supplementary device 200 is shaped so that it attaches to the distal end of the injection device 10 but does not extend beyond the housing 11 of the injection device 10. In this situation the injection device 10 can have a recess, for instance located under a removable cap 30, in which the supplementary device 200 is located upon attachment. Any components of the injection device 10 that need to be exposed during use, such as visual indicators 231, may be located upon the surface of the supplementary device 200 that is still exposed upon attachment, and so effectively this surface forms the distal end of the injection device 10. In some embodiments, the supplementary device 200 has a tear-drop shaped cross section, the tear-drop cross section may include a flexible or rigid extension 280 as discussed herein (FIG. 13C). For instance, the extension 280 may be a flexible PCB that is positioned against the supplementary device 200 when the device is unattached, to form a tear-drop shape, and when preparing the supplementary device 200 for attachment to an injection device 10 can be folded into a position such that the extension 280 is located within a recess or cavity of the injection device 10 upon attachment.

FIG. 3 is a schematic illustration of an embodiment of a supplementary device 200, showing some internal and external components. Internally, the supplementary device 200 comprises primary electronics 24. The primary electronics 24 comprise at least a processor 25. The processor 25 may for instance be a microprocessor, a Digital Signal Processor (DSP), Application Specific Integrated Circuit (ASIC), Field Programmable Gate Array (FPGA) or the like. The processor 25 executes program code (e.g. software or firmware). The primary electronics 24 may, in some embodiments, be located on a flex PCB.

The supplementary device 200 may comprise memory. The primary electronics 24 may comprise both a program memory and a main memory. The processer may execute program code stored in the program memory, and uses a main memory, for instance to store intermediate results. The program memory may for instance be a Read-Only Memory (ROM), and the main memory may for instance be a Random Access Memory (RAM). The device may comprise non-volatile memory for the storage of information, for instance information derived from any sensors comprised within the supplementary device 200.

The supplementary device 200 also comprises one or more sensors. The one or more sensors may be coupled to and controlled by the primary electronics 24.

The supplementary device 200 also comprises a communication unit, which is configured to transmit and/or receive information to/from another device. The communication unit 240 may be a wireless unit 241. Such transmission may for instance be based on radio transmission or optical transmission. In some embodiments, the wireless unit 241 is a Bluetooth transceiver. Alternatively, wireless unit 241 may be substituted or complemented by a wired unit (not shown) configured to transmit and/or receive information to/from another device in a wire-bound fashion, for instance via a cable or fibre connection. When data is transmitted, the units of the data (values) transferred may be explicitly or implicitly defined. The wireless unit 241 may be coupled to and controlled by the primary electronics 24. In a particular example, the external device 1000 may active the supplementary device 200 by near-field communication (NFC), in this example the supplementary device 200 will comprise a near-field communication antenna 242. In some examples, the supplementary device 200 will comprise a communication unit 240 capable of both Bluetooth communication and NFC.

The supplementary device 200 may comprise components 230 for providing feedback to a user. For instance, the supplementary device 200 may comprise one visual indicator 231, such as an LED 232, or a plurality of visual indicators 231. The visual indicator 231 may emit light to indicate a particular state to the user. If the device comprises a plurality of visual indicators 231, the particular combination of indicators emitting light may indicate different statuses. Alternatively, or in addition, an individual visual indicator 231 may have different outputs or displays depending on the status being indicated. For instance, the visual indicator 231 may output light of different colours to indicate different statuses. One or more visual indicator may be an RGB LED 233.

The supplementary device 200 may also comprise one or more audible indicator 234, such as an audio module 104 configured to provide audio feedback to a user of the supplementary device 200. The one or more audible indicator 234 may, for instance, be a speaker, buzzer, piezo beeper, or any suitable audible indicator. This may be an alternative to the visual indicators 231, or may be in addition to the visual indicators 231. Both the one or more visual indicator 231 and the one or more audible indicators 234 may be coupled to and controlled by the primary electronics 24.

The supplementary device 200 may optionally comprise a locking sensor 106 configured to sense whether the attachment mechanism is in the locked position or the unlocked position.

As will be discussed further below, the components 230 for providing feedback to a user may be used to provide information on the start of an injection, for instance the failure to detect a start of an injection, the end of an injection, for instance the failure to detect the end of an injection, or data transmission status, for instance successful or unsuccessful data transmission.

The supplementary device 200 may comprise a power supply 212, such as a battery. The power supply 212 may supply power to the electrical components of the supplementary device 200, for instance the primary electronics 24, the memory 34, the wireless unit 241, the one or more sensors, the visual indicators 231, and/or the audible indicators 234.

Figure 4:
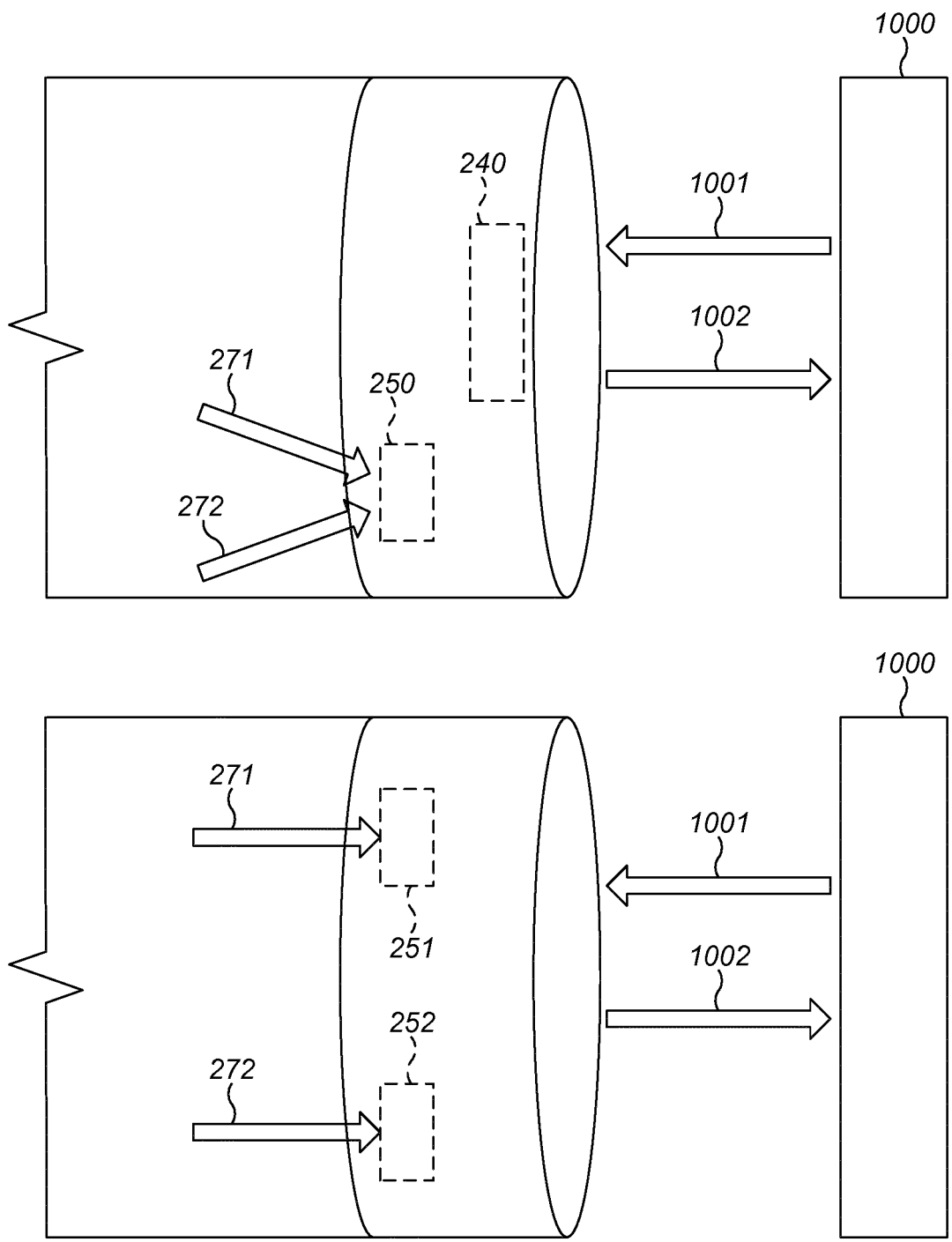
FIG. 4 shows the communication between an embodiment of the supplementary device, an injection device, and an external device.

FIG. 4 is illustrates an exemplary system and shows the communication between the supplementary device 200 and other devices.

The supplementary device 200 has a resting state, in which the electronic components may be in a low-power mode wherein all non-essential electrical processes are powered down. For instance, if the supplementary device 200 comprises sensors, audible indicators 234, or visual indicators 231, in the resting state these components would not be active or powered. This has the advantage of minimizing the power consumption of the supplementary device 200.

The supplementary device 200 may be activated, that is brought out of the resting state into an active state, by signals 1001 received from an external device 1000. The signals 1001 may comprise a wake-up signal. The external device 1000 may activate the supplementary device 200 by signals sent via any suitable means, including wired or wireless connections, and communicated to the communication unit 240 of the supplementary device 200. The communication unit 240 of the supplementary device 200 may be such that it is capable of receiving the signal while the supplementary device 200 is in the low-power mode, for instance either by not requiring a separate power supply or by maintaining access to the power supply of the supplementary device 200 while in the low-power mode. In a particular example, an external device may activate the supplementary device 200 by near-field communication, in this example the supplementary device 200 will comprise a near-field communication antenna 242.

Once activated, the supplementary device 200 may be in an active state. In this state, for instance, any sensor or sensors may be capable of detection. The supplementary device 200 may, in this state, be capable of transferring data to the external device 1000.

The injection device 10 is capable of administering an injection regardless of the status of the supplementary device 200. For instance, the injection device 10 may be an autoinjector, which is capable of delivering an injection with the supplementary device 200 unattached or attached, or when the supplementary device 200 is in the resting state or the active state.

The external device 1000 may be any device capable of communicating with the supplementary device 200, and of storing, processing, displaying, or transmitting data received from the supplementary device 200. For instance, the external device 1000 may be a tablet, a smartphone, a smart watch, a computer, or any suitable device.

The supplementary device 200 and/or the injection device 10 may comprise at least one sensor 251 capable of detecting the start of an injection 271 by the injection device 10. The sensor 251 may include a switch, a conductive rubber pad, a hall effect sensor, a piezoelectric sensor, an optical sensor, or any suitable sensor. The sensor 251 may be capable of detecting the movement of a part of the injection device 10 that is associated with the injection itself, for instance the sensor 251 may detect the movement of a plunger 14 or of a component linked to or associated with the plunger. To detect the start of an injection the sensor 251 may detect the start of the movement of the aforementioned component.

For instance, the sensor 251 may be a conductive rubber pad 260 comprised within the supplementary device 200 which, when the supplementary device 200 is attached to the injection device 10, may be configured to detect the movement of a component of the injection device 10 that is involved in the injection procedure. Hence, the conductive rubber pad 260 may be capable of detecting the start of an injection procedure by the injection device 10. The rubber pad 260 may be located so that when the supplementary device 200 is attached to the injection device 10 a projection from the plunger, or an associated component, is pressed against the conductive rubber pad. This projection is configured to retract into the injection device 10 as the plunger progresses, so once an injection has started the projection is no longer pressed into the rubber pad. Alternatively or in addition, the conductive rubber pad 260 may be positioned on a rigid or flexible extension 280 as described herein, for instance a flexible PCB, to allow the positioning of the conductive rubber pad 260 in a location to allow the determination of information in relation to the injection device 10 when the supplementary device 200 is attached to the injection device 10.

Figure 5A:
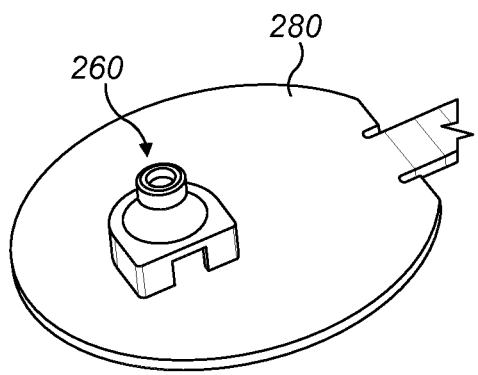
FIG. 5A shows an embodiment of the supplementary device comprising a conductive rubber pad.
Figure 5B:
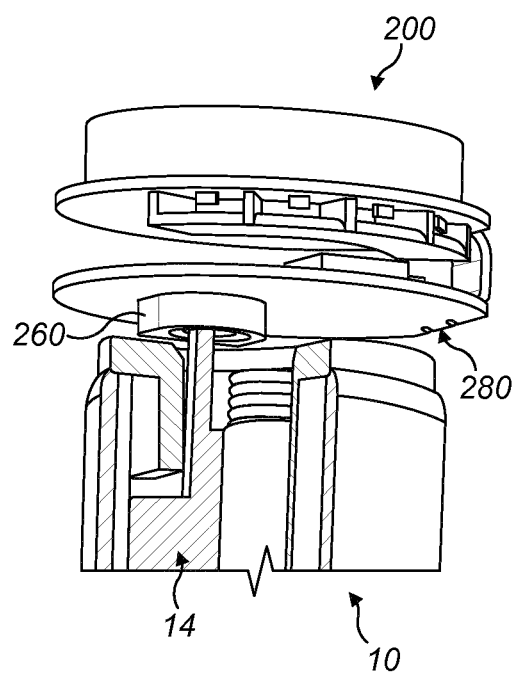
FIG. 5B shows an embodiment of the supplementary device comprising a conductive rubber pad during use with an injection device to detect the start of an injection procedure.
Figure 5C:
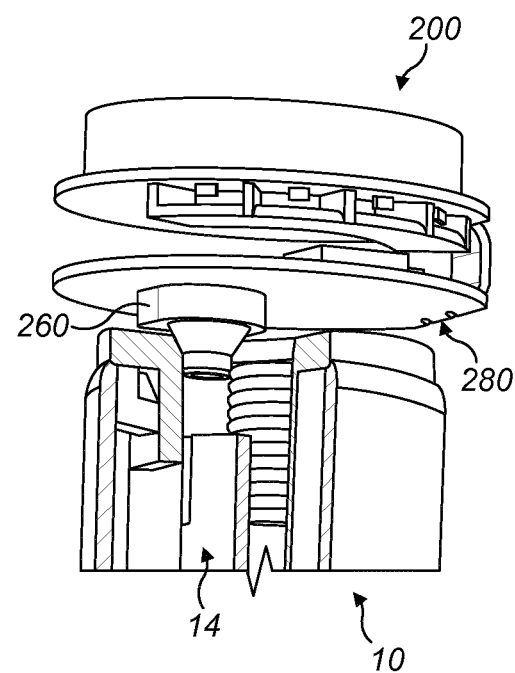

The conductive rubber pad 260 may be as depicted in FIG. 5A. The rubber pad comprises a protrusion which, when the supplementary device 200 is attached to the injection device 10, is located so as to be pressed into the pad and to be in a stressed state (FIG. 5B). The protrusion is forced into this position by either a part of the plunger 14, such as a projection from the plunger 14, or a component attached to, or associated with, the plunger. When the plunger moves (FIG. 5C), the part pressing onto the protrusion of the rubber pad moves away from the rubber pad, and so releases the protrusion, allowing the protrusion to relax away from the rubber pad. This movement therefore can be detected, and allows the determination of the start of an injection.

Alternatively, or in addition, the sensor may be a switch that is configured to detect the movement of a component of the injection device 10 that is involved in the injection procedure. The switch may be a micro-switch 261. The switch may be comprised within the supplementary device itself. Alternatively, the switch or micro-switch 261 may be located within the injection device 10, and may communicate the start of the injection procedure to the supplementary device 200. This communication may be via any suitable means, for instance a wired connection. Alternatively or in addition, the switch or micro-switch 261 may be positioned on a rigid or flexible extension 280 as described herein, for instance a flexible PCB, to allow the positioning of the switch or micro-switch 261 in a location to allow the determination of information in relation to the injection device 10 when the supplementary device 200 is attached to the injection device 10.

Figure 6A:
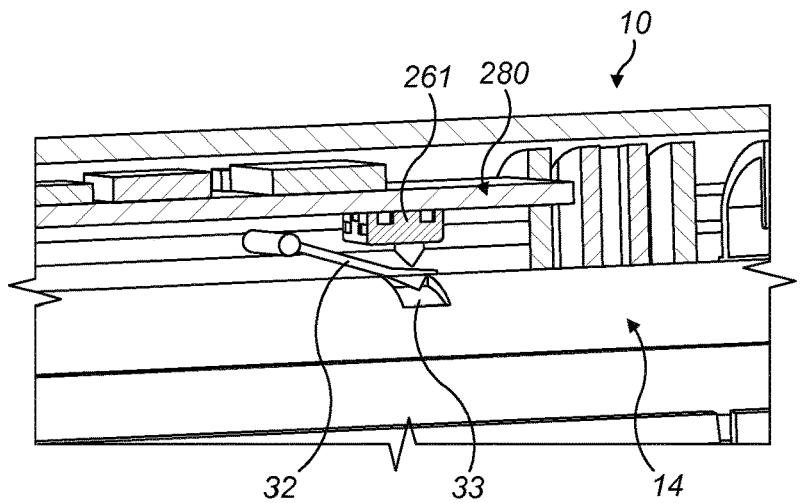
FIG. 6A shows an embodiment of the supplementary device comprising a micro-switch before an injection procedure.
Figure 6B:
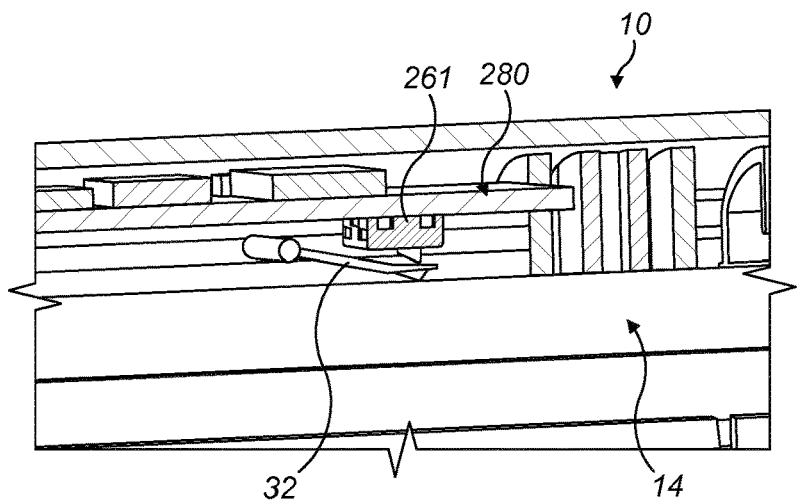
FIG. 6B shows an embodiment of the supplementary device comprising a micro-switch during an injection procedure.

In an embodiment, the micro-switch 261 may be as depicted in FIG. 6. The micro-switch is located within the supplementary device 200, but can detect the movement of a lever 32 located within the injection device 10. The lever 32 may be located before the start of an injection procedure within a slot or gap 33 within the plunger (FIG. 6A), and may be biased towards the slot or gap 33. Alternately, the lever 32 may be located within and biased towards a slot or gap 33 of a component attached to the plunger so as to move with the plunger. Upon movement of the plunger, or plunger-associated component, the lever 32 may be forced out of the slot or gap 33, and the micro-switch may detect this movement in order to determine the start of an injection (FIG. 6B).

Alternatively, or in addition, the sensor may be an optical reflecting sensor 263. This sensor 263 may be capable of sensing the movement of a component of the injection device 10 that is involved in the injection procedure. For instance, the optical reflecting sensor 263 may be capable of sensing continuously the movement of a plunger 14. To facilitate this detection, the plunger of the injection device 10 may be patterned or coded to allow particular portions of the plunger 14 to be identified. The optical reflecting sensor 263 may be comprised within the supplementary device 200 itself. Alternatively, the optical reflecting sensor 263 may be located within the injection device 10, and may communicate the start of the injection procedure to the supplementary device 200. This communication may be via any suitable means, for instance a wired connection. Alternatively or in addition, the optical reflecting sensor 263 may be positioned on a rigid or flexible extension 280 as described herein, for instance a flexible PCB, to allow the positioning of the optical reflecting sensor 263 in a location to allow the determination of information in relation to the injection device 10 when the supplementary device 200 is attached to the injection device 10.

Figure 7A:
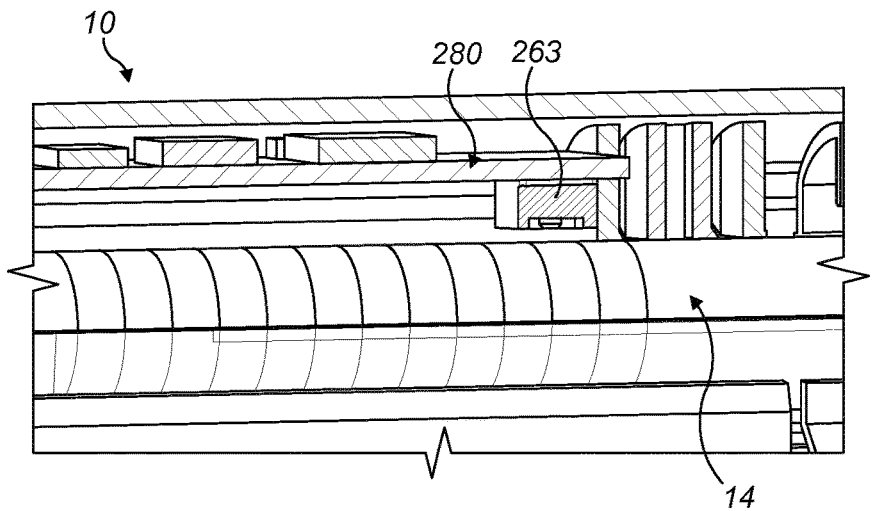
FIG. 7A shows an embodiment of the supplementary device comprising an optical reflecting sensor before an injection procedure.
Figure 7B:
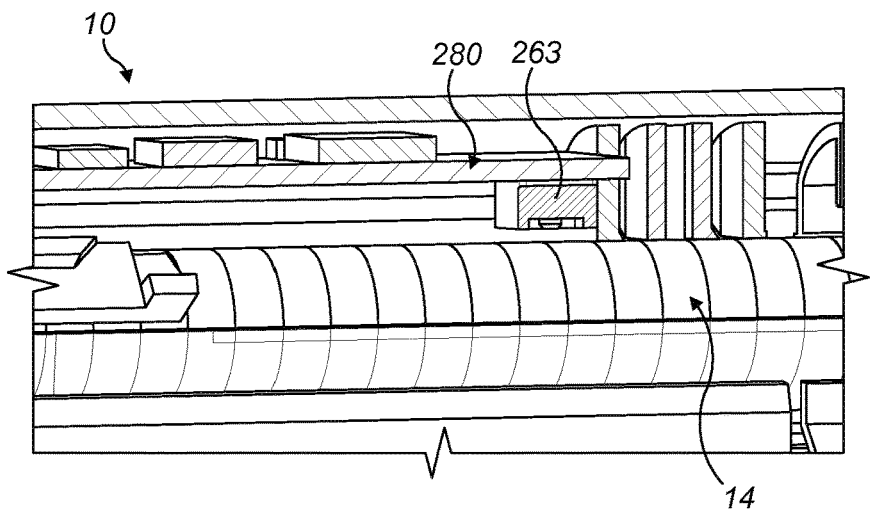
FIG. 7B shows an embodiment of the supplementary device comprising an optical reflecting sensor during an injection procedure.

FIG. 7A shows an example supplementary device 200, comprising an optical reflecting sensor 263, attached to an injection device 10 before the initiation of an injection procedure. In this example, once the injection procedure has been initiated (FIG. 7B), the optical reflecting sensor 263 can continuously detect the progress of the injection as the plunger moves past the sensor because the plunger includes alternating sections with distinct optical properties that can be detected by the sensor. Once the injection has ended (FIG. 7C) the sensor can detect the end of an injection either because the alternating sections are no longer progressing past the sensor, or because the final section of the plunger that is positioned to be detected by the sensor has a unique optical property allowing its identification.

If the supplementary device 200 does not detect the start of an injection, within a pre-determined time after the supplementary device 200 has been activated by the external device 1000, the supplementary device 200 may inform the user via any feedback means as disclosed herein.

The at least one sensor capable of detecting the start of an injection can communicate this information to a processor 25 or controller comprised within the supplementary device 200.

The supplementary device 200 and/or the injection device 10 may comprise at least one sensor 250 capable of detecting the end of an injection 272 by the injection device 10. This sensor 250 may also be capable of sensing the start of an injection 271, as discussed above. Alternatively, there may be multiple sensors, for instance a sensor 251 for detecting the start of the injection procedure 271 and a separate sensor 252 for detecting the end of the injection procedure 272. The sensor 250 may be capable of detecting the movement of a part of the injection device 10 that is associated with the injection itself, for instance the sensor may detect the movement of a plunger 14 or of a component linked to or associated with the plunger. To detect the end of an injection 272 the sensor 250 may detect the end of the movement of the aforementioned component, or may detect the movement of the component into a position associated with the end of an injection. For instance, the sensor 250 may detect when a plunger has moved the full length required for an injection.

The sensor 250 may include a switch, a conductive rubber pad, a hall effect sensor, a piezoelectric sensor, an optical sensor, or any suitable sensor.

The sensor 250 may be a switch that is configured to detect the position or movement of a component of the injection device 10 that is involved in the injection procedure. The switch may detect the movement of the component, for instance a plunger or component associated with the plunger, into a position associated with the end of an injection. For instance, the switch may detect when the plunger has moved the full length required for an injection. The switch may be a micro-switch 261. The switch may be comprised within the supplementary device 200 itself. Alternatively, the switch or micro-switch 261 may be located within the injection device 10, and may communicate the start of the injection procedure to the supplementary device 200. This communication may be via any suitable means, for instance a wired connection. The switch or micro-switch 261 may be positioned on a rigid or flexible extension 280 as described herein, for instance a flexible PCB.

Figure 6C:
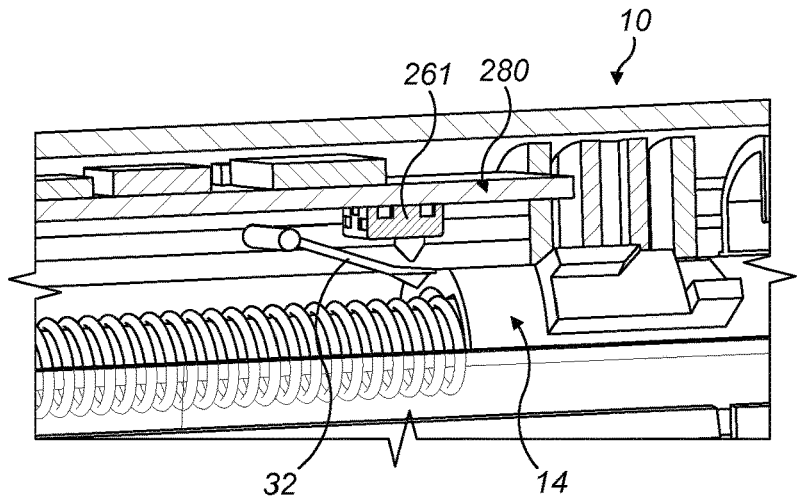
FIG. 6C shows an embodiment of the supplementary device comprising a micro-switch at the end of an injection procedure.

In an embodiment, the micro-switch 261 may be as depicted in FIG. 6. During an injection procedure the micro-switch 261 may be activated by a lever 32 as shown in FIG. 6B, which has been forced by the plunger 14 into an activated position wherein the lever 32 is biased against the plunger 14. At the end of an injection procedure, the plunger 14 will move into a position wherein the lever 32 is able to move into a relaxed positon, hence no longer activating the micro-switch 261 (FIG. 6C) and allowing the end of an injection procedure to be determined 272.

The at least one sensor 250 capable of detecting the end of an injection 272 by the injection device 10 may be a conductive rubber pad 260, which is positioned such that the movement of a component into a position associated with the end of an injection is detected. The conductive rubber pad 260 may be positioned on a rigid or flexible extension 280 as described herein, for instance a flexible PCB.

Figure 7C:
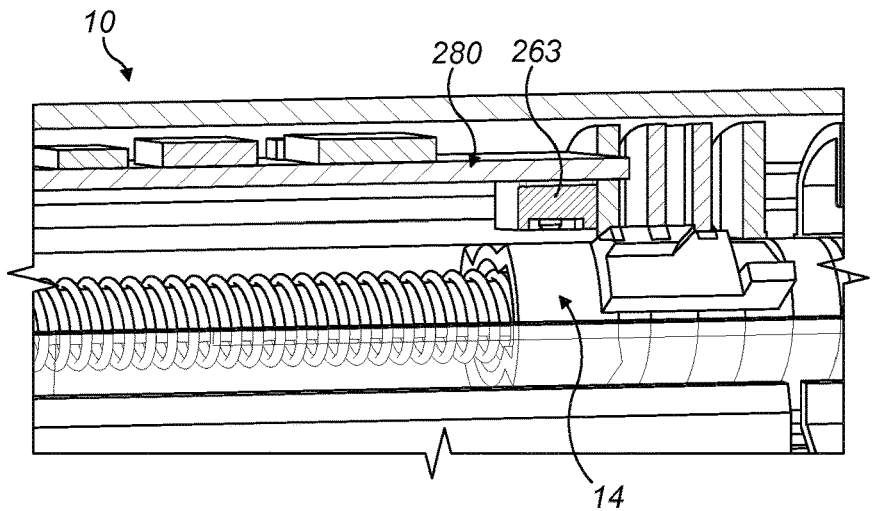
FIG. 7C shows an embodiment of the supplementary device comprising an optical reflecting sensor at the end of an injection procedure.

Alternatively, or in addition, the sensor 250 may be an optical reflecting sensor 263. This sensor 263 may be capable of sensing the movement of a component of the injection device 10 that is involved in the injection procedure. For instance, the optical reflecting sensor may be capable of sensing continuously the movement of a component associated with an injection, for instance a plunger, and detecting when this movement comes to an end 272. Alternatively, the optical reflecting sensor may be able to sense when a portion of the aforementioned component reaches a predetermined position associated with the end of an injection (FIG. 7C). For instance, the optical reflecting sensor may be able to detect when a portion of a plunger moves into a position that indicates that the plunger has moved the full length required for an injection. To facilitate these detections, the plunger of the injection device 10 may be patterned or coded to allow particular portions of the plunger to be identified. The optical reflecting sensor may be comprised within the supplementary device 200 itself. Alternatively, the optical reflecting sensor may be located within the injection device 10, and may communicate the start of the injection procedure to the supplementary device 200. This communication may be via any suitable means, for instance a wired connection. The optical reflecting sensor 263 may be positioned on a rigid or flexible extension 280 as described herein, for instance a flexible PCB, to allow the positioning of the optical reflecting sensor 263 in a location to allow the determination of information in relation to the injection device 10 when the supplementary device 200 is attached to the injection device 10.

If the supplementary device 200 does not detect the end of an injection 272, within a pre-determined time after the supplementary device 200 has been activated by the external device 1000, the supplementary device 200 may inform the user.

The at least one sensor 250 capable of detecting the end of an injection can communicate this information to a processor 25 or controller comprised within the supplementary device 200.

The supplementary device 200 may comprise a sensor 251 to detect the start of an injection, and a separate sensor 252 to detect the end of an injection. Alternatively, the supplementary device 200 may comprise a single sensor 250 able to determine both the start and end of an injection. As a third alternative, the supplementary device 200 may comprise a sensor 263 able to continuously detect the progress of an injection procedure.

The supplementary device 200 may be capable of determining information about the medicament within the injection device 10, for instance via a sensor 253. For example, the supplementary device 200 may be capable of determining the type of medicament, identity of the medicament, ID number, batch number, expiry date, elapsed time, or similar information. The supplementary device 200 may comprise a sensor 254 capable of determining an optical property of a portion of the injection device 10, or a component associated with or attached to the injection device 10 such as a medicament cartridge, in order to determine the medicament related information. Alternatively, or in addition, the sensor 253 may be capable of detecting a code from which medicament related information can be derived.

The supplementary device 200 may comprise an optical sensor 254 capable of determining information about the medicament within the injection device 10. For instance, the information 100 identifying the medicament may be the colour of the housing 11 of the injection device 10, or the colour of an area of the housing or a label affixed to the housing. In these embodiments, the optical sensor 254 may be a simple photometer configured to detect the colour. In some other embodiments, the information 100 identifying the medicament may be a QR code, or other similar encoded information and the optical sensor 254 may be a camera or QR code reader. Further, one or more light sources may be provided to improve reading of optical sensor 254. The light source may provide light of a certain wavelength or spectrum to improve colour detection by optical sensor 254. The light source may be arranged in such a way that unwanted reflections, for example due to the curvature of the housing 11, are avoided or reduced. In an example embodiment, the optical sensor 254 is a camera unit configured to detect a code 100 (for instance a bar code, which may for instance be a one- or two-dimensional bar code) related to the injection device 10 and/or the medicament contained therein. This code 100 may for instance be located on the housing 11 or on a medicament container contained in injection device 10, to name but a few examples. This code 100 may for instance indicate a type of the injection device 10 and/or the medicament, and/or further properties (for instance an expiration date). This code 100 may be a QR code 100. The QR code is in general black and white and thus no colour detection is required on the part of the optical sensor 254. This allows the optical sensor 254 to be simple and cheap to manufacture. In other embodiments, the supplementary device 200 may comprise a sensor (not shown) capable of determining information about the medicament within the injection device 10 via other means, such as the detection of an RFID.

The processor 25 may be configured to check the information 100 read by the sensor 253 against pre-stored information, for instance in order to verify that the user is injecting the correct medicament. If the processor 25 does not recognise the information 100 or recognises the information 100 as indicating that the injection procedure may be inappropriate, for instance if the information were to indicate a different medicament to that which the user should be receiving at that time, then the supplementary device 200 may produce an alarm signal. The alarm signal may comprise use of any of the feedback methods as disclosed herein, including indicators 230 associated with the supplementary device 200 or communication to an external device 1000 which can display information to the user.

Optionally, the supplementary device 200 may include a temperature sensor 255. The temperature sensor 255 may detect the temperature of the supplementary device 200 itself, and this information can be used to estimate the temperature of the medicament present in the injection device 10. A flow chart illustrating operations that can be performed by a supplementary device 200 comprising a temperature sensor 255 is show in FIG. 8.

The temperature sensor 255 may be positioned on a rigid or flexible extension 280 as described herein, for instance a flexible PCB, to allow the positioning of the temperature sensor 255 in a location suitable for estimating the temperature of the medicament present in the injection device 10.

The temperature sensor 255 may begin detection after the supplementary device 200 has been activated 601, and so the temperature sensor 255 may be activated in the active state of the supplementary device 200. After activation the temperature sensor 255 may determine the temperature 602.

It is preferable to deliver medicament at a particular temperature, for instance room temperature, as injection of medicament that is too cold or too hot may be uncomfortable for the user. However, some medicaments are stored at low temperatures. Hence, the supplementary device 200, upon determining that the temperature is lower than a predetermined temperature 603, such as room temperature, may inform the user that the medicament is not at the correct temperature 604. When the correct temperature is reached, the supplementary device 200 may inform the user 605. The feedback methods may be any as disclosed herein, including indicators 230 associated with the supplementary device 200 or communication to an external device 1000 which can display information to the user.

Figure 9:
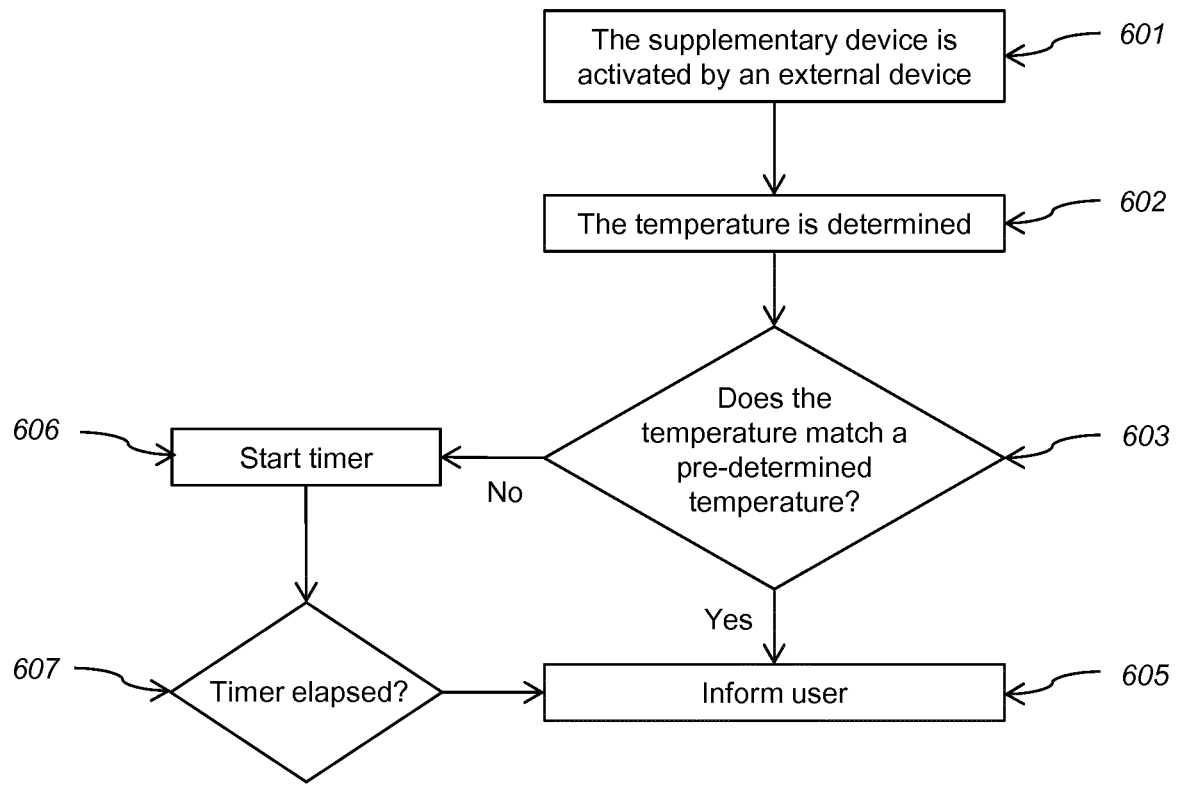
FIG. 9 shows a flowchart illustrating operations which can be performed by an embodiment of the supplementary device in relation to temperature determination.

Alternatively, or in addition, the supplementary device 200 upon detection of the ambient or incorrect temperature may start a timer 606 as illustrated in FIG. 9. The timer may run for the length of time required for medicament to reach the required temperature. This length of time may be adjusted depending on the type or identity of the medicament, or other properties such as volume of medicament. Once the time has elapsed 607, the user can be informed 605, either by indicators 230 associated with the supplementary device 200 or by communication to an external device 1000 which can display information to the user.

Figure 10:
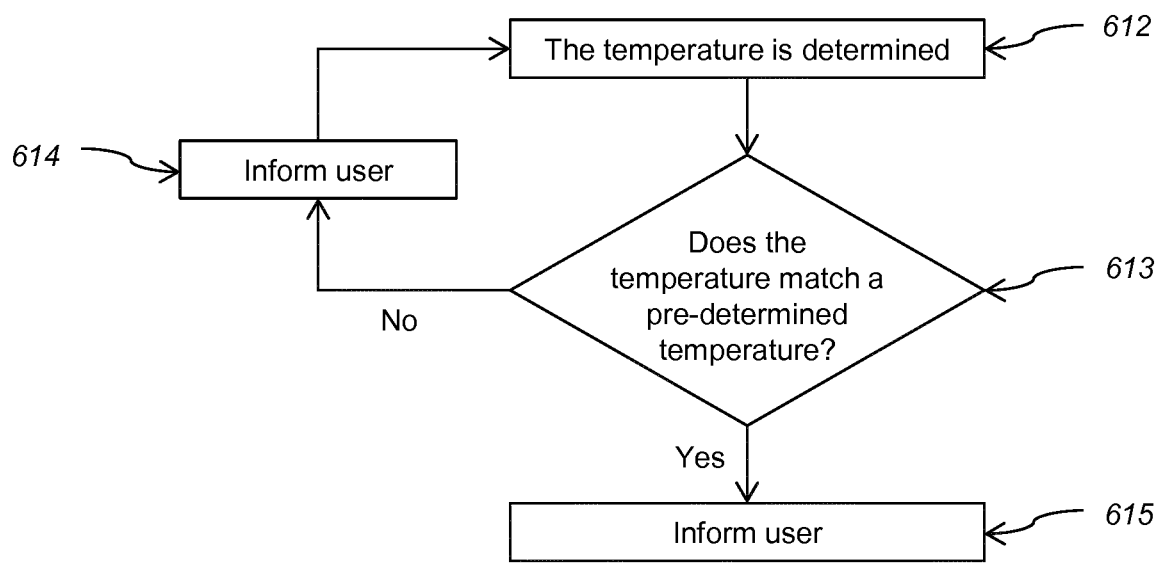
FIG. 10 shows a flowchart illustrating operations which can be performed by an embodiment of the supplementary device in relation to temperature determination.

In other embodiments, the supplementary device 200 may comprise a temperature sensitive patch, capable of determining the temperature 612 (see FIG. 10). The temperature sensitive patch may be configured to indicate when the temperature is either unsuitable for an injection 614 and/or suitable for an injection 615, based upon whether the ambient temperature matches a predetermined temperature 613. For instance, the temperature sensitive patch may be a particular colour, such as red, when the temperature is unsuitable. In other examples, the temperature sensitive patch may be a different colour, for instance green, when the temperature is suitable. This allows the user to determine whether or not the temperature of the medicament is suitable for the injection procedure to be started.

The temperature sensor 255 may provide information to the processor 25 of the supplementary device 200. The processor 25 may process and transmit the received information, for instance via the communication unit 240 to an external device 1000. Alternatively, or in addition, the processor 25 of the supplementary device 200 may be able to use a specific algorithm in order to ascertain the temperature of medicament within an injection device 10 based upon the information provided. This information may be transmitted, for instance via the communication unit 240 to an external device 1000. In other embodiments, the information received by the processor 25 will be processed and transmitted to the external device 1000, and any calculations, including the estimation of the temperature of the medicament within the injection device 10, will be performed by the external device 1000.

The communication of the temperature sensor 255 information to an external device 1000 may be via any method, or concurrent with any transmission, as disclosed herein.

The communication unit 240 is able to transmit data 1002 to an external device 1000; the transmission may be via any suitable means such as wired or wireless communication. The external device 1000 may be the same external device used to activate the supplementary device 200. The transfer may be activated by near-field communication, and/or the transfer may proceed via near-field communication. In some embodiments the data transfer will be via Bluetooth. In other embodiments, near-field communication will be used to activate the supplementary device 200, and Bluetooth will be used to transmit the gathered information. The supplementary device 200 may be capable of sensing whether the data transfer has been successful, or has been completed, and if not the supplementary device 200 may either retry the transmission and/or inform the user of the failure to transmit the data.

The data transmitted may include information on the start of the injection, the end of the injection, temperature, and/or medicament related information.

In some embodiments the data will be transmitted after the start of the injection has been detected, in other embodiments the data will be transmitted after the end of the injection has been detected. The user may be informed by any means or method as disclosed herein.

Optionally, the supplementary device 200 may comprise memory 34 suitable for the storage of the information determined by the sensors. This information may include information relating to the start of injection, the end of injection, medicament, temperature, or any other derived information. The data to be transmitted to the external device 1000 may be the data stored within the memory 34.

The external device 1000 may be capable of processing and displaying the information received. The external device 1000 may be able to transmit the data to a third party device, such as cloud services.

The external device 1000 may, before the start of an injection, display warnings or alerts to the user, for instance those discussed herein in relation to the medicament identity. The external device 1000 may also, or alternatively, display instructions for the advised treatment.

After the injection, the external device 1000 may, based on the received information, display information or instructions, such as history logs, date of next dose, indications on treatment, and the like.

Figure 11:
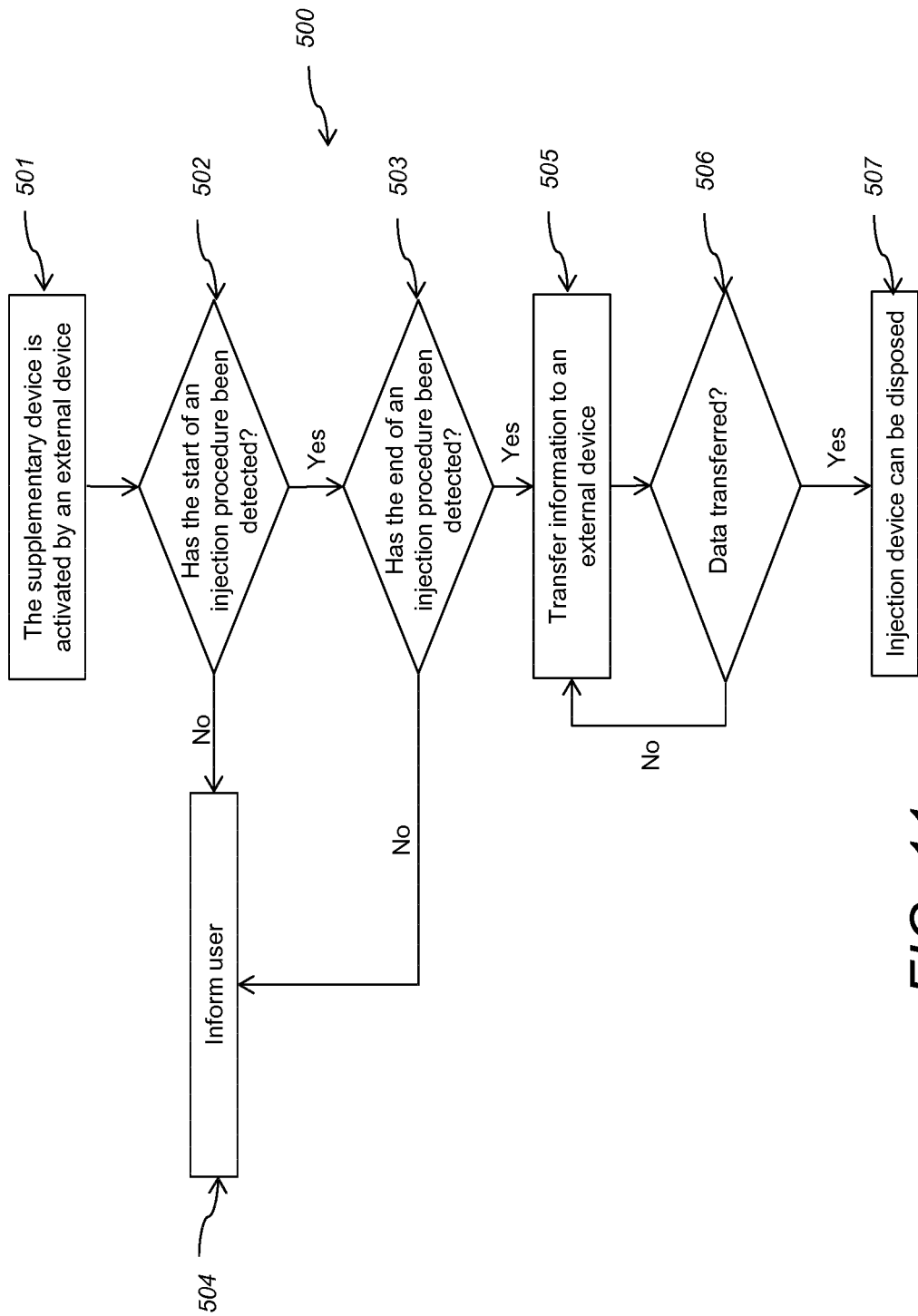
FIG. 11 shows a flowchart illustrating operations which can be performed by an embodiment of the supplementary device in relation to determining the start and end of an injection procedure, and transferring data in relation to this determination to an external device.

FIG. 11 shows a flow chart illustrating operations which can be performed by an illustrative embodiment of the supplementary device 200. This embodiment is a supplementary device 200 that comprises a near-field communication antenna 242, a sensor 251 for detecting the start of an injection procedure by a disposable autoinjector, optionally a separate sensor 252 for detecting the end of an injection procedure, a processor 25, and hooks 211 configured to attach the supplementary device 200 onto a disposable autoinjector in a predetermined position.

The sensors of this embodiment are configured to detect, via separate components, the start of an injection and the end of an injection. The start of the injection is detected by a conductive rubber pad 260 as show in FIG. 5 and described herein. The end of the injection can be detected by any means or sensor as disclosed herein.

The supplementary device 200 of this embodiment operates as follows. The supplementary device 200 is connected to a disposable pen autoinjector via hooks 211 which snap into recesses 31 comprised by the autoinjector, thus attaching the supplementary device 200, and hence the sensors, in a predetermined position. The supplementary device 200 attaches in a manner that the resultant assembly is of an extended length compared to the injection device 10 alone. After attachment, the electronics of the supplementary device 200 are then activated by an external device 1000, such as a smartphone, via near-field communication (step 501). This activates the sensors, including both the start-of-injection sensor 251 and the end-of-injection sensor 252.

The supplementary device 200 of this embodiment also comprises a temperature sensitive label as described herein. The temperature sensitive label will indicate to the user whether the medicament is at the appropriate temperature for injection, as illustrated in FIG. 10 and described herein. If the temperature is not the appropriate temperature the user will wait until the patch indicates that the temperature is the correct temperature before beginning the injection procedure.

After activation if the start-of-injection sensor 251 does not detect the start of an injection within a pre-determined time 502, the user is informed 504. If the sensor detects the start of an injection step 502, this is communicated to the processor 25. Subsequently, if the end-of-injection sensor 252 does not detect the end of an injection within the pre-determined time 503, the user is informed 504. If the end-of-injection sensor 252 does detect the end of an injection 503, this is communicated to the processor 25. The processor 25, upon receipt of the start and end of injection information, is then able to transmit the information via the communication unit 240 to the external device 1000 via near-field communication 505. This transmission is activated by a communication 1001 received from the external device 1000 via near-field communication or Bluetooth low energy. If information transmission fails, or is incomplete, the supplementary device 200 will re-transmit the information 506.

Based on the data received, the external device 1000 displays instructs and information to the user based upon the device usage history. The autoinjector can now be disposed 507.

The supplementary device 200 of this embodiment may not detect the end of the injection, and in this case will only comprise the sensor 251 for detecting the start of the injection. In this situation the method of operation will be as described herein, but lacking the steps in relation to the detection of the end of the injection.

FIG. 11 shows a flow chart illustrating operations which can be performed by an illustrative embodiment of the supplementary device 200. This embodiment is a supplementary device 200 that comprises a communication unit 240 that can communicate via BLE whisper mode, a sensor 250 for detecting the start and end of an injection procedure by a disposable autoinjector, a processor 25, and hooks 211 configured to attach the supplementary device 200 onto a disposable autoinjector in a predetermined position. The supplementary device 200 also includes an extension 280 that is a flexible PCB which can extend outwardly from the body of the supplementary device 200. When attached to the injection device this flexible PCB will be positioned within the housing of the injection device and will extend along the injection device in a perpendicular direction (illustrated by FIG. 13B). The supplementary device 200 further comprises a multi-coloured LED 233, allowing feedback to the user.

The sensor 250 of this embodiment is configured to detect, via a single micro-switch 261, both the start and end of an injection by the movement of the plunger of the injection device 10. The sensor 250 is located on the flexible PCB such that, upon attachment to an injection device, the micro-switch 261 is positioned as shown in FIG. 6. The sensor is configured to communicate this information to the processor 25 comprised within the supplementary device 200.

The supplementary device 200 of this embodiment operates as follows. The supplementary device 200 is connected to a disposable pen autoinjector via hooks 211 which snap into recesses 31 comprised by the autoinjector, thus attaching the supplementary device 200, and hence the sensors, in a predetermined position. The electronics of the supplementary device 200 are then activated by an external device 1000, such as a smartphone, via near-field communication, this is step 501. This activates the sensor 250 for detecting the start and end of an injection procedure.

The supplementary device 200 of this embodiment also comprises a temperature sensitive label as described herein. The temperature sensitive label will indicate to the user whether the medicament is at the appropriate temperature for injection, as illustrated in FIG. 10 and described herein. If the temperature is not the appropriate temperature the user will wait until the patch indicates that the temperature is the correct temperature before beginning the injection procedure.

After activation, if the sensor 250 does not detect the start of an injection within a pre-determined time 502, the user is informed 504 via the multi-coloured LED 233. If the sensor 250 detects the start of an injection 502, this is communicated to the processor 25. Subsequently, if the sensor 250 does not detect the end of an injection within a pre-determined time 503, the user is informed 504 via the multi-coloured LED 233. If the sensor 250 does detect the end of an injection 503, this is communicated to the processor 25. The processor 25, upon receipt of the start and end of injection information, is then able to transmit the information via the communication unit 240 to the external device 1000 via near-field communication 505. This transmission is activated by a communication received from the external device 1000 via near-field communication. If information transmission fails, or is incomplete, the supplementary device 200 will re-transmit the information 506.

Based on the data received, the external device 1000 displays instructs and information to the user based upon the device usage history. The autoinjector can now be disposed 507.

FIG. 11 shows a flow chart illustrating operations which can be performed by an illustrative embodiment of the supplementary device 200. This embodiment is a supplementary device 200 is able to communication with external devices by both NFC and Bluetooth. The supplementary device 200 also comprises a temperature sensor 255, a sensor 253 for identifying the medicament identity, and a plurality of LEDs 232 for indicating the device status to the user, and a processor 25. The supplementary device 200 itself has a tear-drop cross-section and is configured to be attached to the distal end of a disposable autoinjector (illustrated by FIG. 13C). The supplementary device 200 also includes an extension 280 that is a flexible PCB which can extend outwardly from the body of the supplementary device 200. When attached to the injection device this flexible PCB will be positioned within the housing of the injection device and will extend along the injection device in a perpendicular direction.

The supplementary device 200 comprises an optical reflecting sensor 263 that is capable of continuously detecting the progress of the injection procedure, as depicted in FIG. 7 and described herein. The optical reflecting sensor 263 is located on the flexible PCB such that, upon attachment to an injection device, the optical reflecting sensor 263 is positioned as shown in FIG. 7. The supplementary device 200 is designed for use with an autoinjector that has a plunger 14, or component associated with a plunger, wherein the optical properties of at least a portion of the plunger enable the position of the plunger to be determined. In this example, the sensor 263 is able to monitor movement of the plunger of the injection device 10, and the plunger of the injection device 10 has an alternating pattern to assist with the monitoring.

The supplementary device 200 of this embodiment operates as follows. The supplementary device 200 is connected to a disposable pen autoinjector in a predetermined position. The electronics of the supplementary device 200 are then activated 501 by an external device 1000, such as a smartphone, via near-field communication. This activates the sensors comprised by the supplementary device 200.

Figure 12:
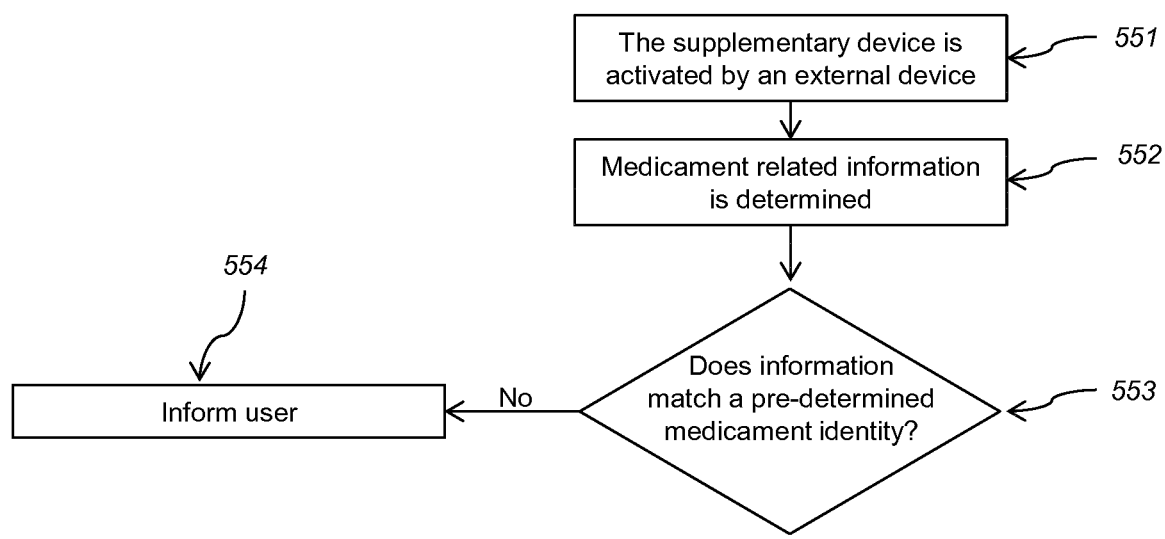
FIG. 12 shows a flowchart illustrating operations which can be performed by an embodiment of the supplementary device in relation to determining medicament related information.

The supplementary device 200 may then determine the identity of the medicament within the disposable autoinjector by any means as disclosed herein. If the medicament identity does not match a pre-determined medicament identity, the supplementary device 200 will alert the user, for instance by illuminating a specific pattern of LEDs or by displaying specific colours via one or more LED. This is depicted by FIG. 12, wherein the supplementary device 200, is activated 551 so that the medicament-information-determining sensor 253 is activated, allowing the determination of medicament related information 552. The supplementary device 200 may then ascertain whether the information matches a pre-determined medicament identity 553. and inform the user of a mismatch 554.

Figure 8:
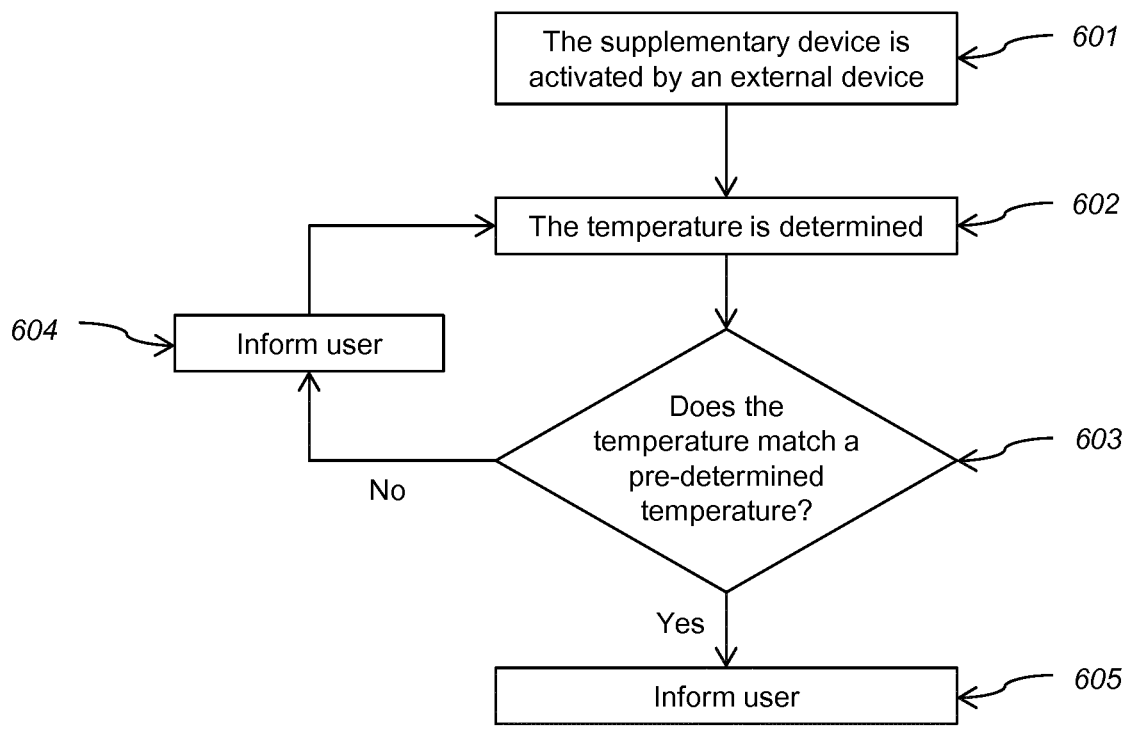
FIG. 8 shows a flowchart illustrating operations which can be performed by an embodiment of the supplementary device in relation to temperature determination.

The supplementary device 200 also determines the ambient temperature via the temperature sensor 255, and calculates an estimated temperature of the medicament within the autoinjector. If the temperature does not match a pre-determined temperature, the supplementary device 200 will alert the user, for instance by illuminating a specific pattern of LEDs or by displaying specific colours via one or more LED. Subsequently, the supplementary device 200 will either indicate to the user that a pre-determined temperature has been detected and so an injection can proceed, or the supplementary device 200 will have activated a timer upon detection of the incorrect temperature and will wait until the timer has elapsed before indicating to the user that an injection can proceed. These processes are depicted in FIG. 8 and FIG. 9 and described herein.

One the start of the injection has been detected by the optical reflecting sensor 263, the injection is monitored continuously by the sensor, allowing both the start 502 and the end 503 of an injection procedure to be determined. The sensor 263 continues to monitor the injection until the end of injection is detected 503, as depicted in FIG. 7 and described herein.

The processor 25, upon receipt of the start and end of injection information, is then able to transmit the information 505 to the external device 1000 via Bluetooth communication. If information transmission fails, or is incomplete, the supplementary device 200 will re-transmit the information 506.

Based on the data received, the external device 1000 displays instructs and information to the user based upon the device usage history. The autoinjector can now be disposed 507.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, ora human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A supplementary device configured to be releasably attached to an injection device, the supplementary device comprising:
   at least one wireless communication unit;
   at least a pair of elongate attachment means for releasably attaching the supplementary device to the injection device; and
   an optical sensor arrangement comprising an extension that extends along a first axis substantially parallel to a longitudinal axis of the injection device and through a distal end of the injection device into a cavity of the injection device when the supplementary device is attached to the injection device such that the optical sensor arrangement is usable to detect a start of an injection by detecting a movement of a part within the injection device, wherein the extension is configured to extend a greater distance along the first axis within the cavity than any distance perpendicular to the first axis, and
   wherein the supplementary device is configured to:
      use the optical sensor arrangement to detect the start of the injection by the injection device, and
      communicate, via the at least one wireless communication unit, the start of the injection to an external device.

2. A supplementary device according to claim 1, wherein the optical sensor arrangement comprises a flexible printed circuit board.

3. A supplementary device according to claim 1, wherein the supplementary device is configured to indicate that the start of the injection by the injection device has not been detected.

4. A supplementary device according to claim 1, wherein the supplementary device is configured to indicate that the start of the injection by the injection device has been detected and that an end of the injection by the injection device has not been detected.

5. A supplementary device according to claim 1, wherein the supplementary device is configured to indicate that the start of the injection by the injection device has been detected and that an end of the injection by the injection device has not been detected within a predetermined time of the start of the injection.

6. A supplementary device according to claim 1, wherein the supplementary device is configured to indicate whether a wireless communication to the external device was successful.

7. A supplementary device according to claim 1, further comprising a temperature sensor.

8. A supplementary device according to claim 7, wherein the supplementary device is configured to indicate whether a medicament included in the injection device meets a predetermined temperature parameter.

9. A supplementary device according to claim 7, wherein the supplementary device is configured to start a timer in response to determining that the medicament included in the injection device does not meet the predetermined temperature parameter and to provide an indication when the timer expires.

10. A system comprising:
an injection device; and
a supplementary device that is configured to be releasably attached to the injection device, the supplementary device comprising:
at least one wireless communication unit,
at least a pair of elongate attachment means for releasably attaching the supplementary device to the injection device, and
an optical sensor arrangement comprising an extension that extends along a first axis substantially parallel to a longitudinal axis of the injection device and through a distal end of the injection device into a cavity of the injection device when the supplementary device is attached to the injection device, such that the optical sensor arrangement is usable to detect a start of an injection by detecting a movement of a part within the injection device, wherein the extension is configured to extend a greater distance along the first axis within the cavity than any distance perpendicular to the first axis, and wherein the supplementary device is configured to:
use the optical sensor arrangement to detect the start of the injection by the injection device, and
communicate, via the at least one wireless communication unit, the start of the injection to the external device.

11. A system according to claim 10, wherein the injection device is a disposable autoinjector.

12. A system according to claim 10, wherein the supplementary device comprises a housing shaped so that, upon attachment to the injection device, the housing of the supplementary device is flush with the housing of the injection device.

13. A system according to claim 10, wherein the system is of uniform width, but greater in longitudinal length than the injection device.

14. A system according to claim 10, wherein the supplementary device is configured to attach within a recess located at the distal end of the injection device.

15. A system according to claim 10, wherein the injection device contains a medicament.

16. A system according to claim 15, wherein the supplementary device further comprises a temperature sensor.

17. A system according to claim 16, wherein the supplementary device is configured to indicate whether the medicament contained in the injection device meets a predetermined temperature parameter.

18. A system according to claim 16, wherein the supplementary device is configured to start a timer in response to determining that the medicament contained in the injection device does not meet the predetermined temperature parameter and to provide an indication when the timer expires.

19. A system according to claim 10, wherein the supplementary device is configured to indicate that the start of the injection by the injection device has not been detected.

20. A system according to claim 10, wherein the supplementary device is configured to indicate that the start of the injection by the injection device has been detected and that an end of the injection by the injection device has not been detected.

* * * * *